United States Patent [19]
Mazac et al.

[11] Patent Number: 5,679,287
[45] Date of Patent: Oct. 21, 1997

[54] USES OF HEPTAFLUOROPROPANE

[75] Inventors: Charles J. Mazac; John S. Rubacha, both of West Lafayette, Ind.

[73] Assignee: Great Lakes Chemical Corporation, West Lafayette, Ind.

[21] Appl. No.: 433,258

[22] Filed: Apr. 28, 1995

[51] Int. Cl.$^6$ .................................................. C09K 15/04
[52] U.S. Cl. .................. 252/399; 252/380; 252/388; 436/8; 436/18; 426/321; 426/541; 426/544; 426/654; 422/40; 422/41; 422/9; 422/10; 206/524.4; 62/78
[58] Field of Search ..................... 62/78; 514/759, 514/672; 252/69, 399, 388, 380; 426/321, 541, 654, 544; 149/109.4; 435/240.1; 436/8, 18; 206/524.9, 524.4; 422/40, 41, 9, 10

[56] References Cited

U.S. PATENT DOCUMENTS

| | | | |
|---|---|---|---|
| 2,868,691 | 1/1959 | Porush et al. | 222/192 |
| 3,282,781 | 11/1966 | Macek et al. | 424/45 |
| 3,955,509 | 5/1976 | Carlson | 149/1 X |
| 4,889,709 | 12/1989 | Mackles et al. | 424/45 |
| 4,971,716 | 11/1990 | Batt et al. | 422/34 |
| 5,118,494 | 6/1992 | Schultz et al. | 424/45 |
| 5,124,053 | 6/1992 | Iikubo et al. | 252/8 |
| 5,230,884 | 7/1993 | Evans et al. | 424/45 |
| 5,292,499 | 3/1994 | Evans et al. | 424/45 |
| 5,314,682 | 5/1994 | Sweval et al. | 424/45 |
| 5,346,669 | 9/1994 | Sweval et al. | 422/34 |
| 5,374,434 | 12/1994 | Clapp et al. | 426/116 |
| 5,443,861 | 8/1995 | Huhne | 427/249 |
| 5,453,445 | 9/1995 | Henry | 514/570 |
| 5,474,759 | 12/1995 | Fassberg et al. | 424/45 |

OTHER PUBLICATIONS

Rev. Metal (Madrid) 1990, vol. 26 No. 3, pp. 143–150 as abstracted by Chemical Abstract No. AN. 1991: 232660.
EP 550031 (Jul. 07, 1993) as Abstracted by Derwent AN. No. 93–215458.
ASC Symp. Ser (1995), (611 Halon Replacements), pp. 122–138 "Compatibility of Halon Alternatives During Storage" as Abstracted by Chemical Ab. 1995: 991871.
WO 92/11190 Jul. 9, 1992.
WO 93/22415 (Nov. 11, 1993).
WO 89/09391 (Oct. 5, 1989).
Sax et al. *Hawley's Condensed Chemical Dictionary,* 11th ed. Van Nostrand Rheinhold Co., NY, NY, 1987, p. 854.

*Primary Examiner*—Sharon Gibson
*Assistant Examiner*—Valerie Fee
*Attorney, Agent, or Firm*—Woodard, Emhardt, Naughton, Moriarty & McNett

[57] ABSTRACT

A method for storing atmosphere sensitive product includes providing an atmosphere surrounding the product which contains at least about 5% heptafluoropropane, preferably at least about 20% heptafluoropropane. The stored products include food, pharmaceutical and chemical products, and mechanical and electrical equipment. In a particular aspect, the method includes storing the product in a closed container and providing in the headspace of the container an atmosphere containing heptafluoropropane.

10 Claims, No Drawings

USES OF HEPTAFLUOROPROPANE

BACKGROUND OF THE INVENTION

1. Field of the Invention

The present invention relates to the containment of various products in a manner to protect the products from degradation and to reduce fire and explosion hazard. More particularly, the present invention relates to novel uses of heptafluoropropane for protecting products from oxygen and other degradation, and for protecting the products and the surroundings from a fire and/or explosion hazard.

2. Description of the Prior Art

Heptafluoropropane has been recently identified in the prior art as having several known uses which take advantage of certain characteristics of the compound. One notable property of heptafluoropropane is that it is not deleterious to the atmosphere ozone layer, in contrast to the chlorofluorocarbons.

Heptafluoropropane has been discovered to be non-flammable and has been found to be useful as a fire extinguishant, either alone or in combination with other extinguishants. Certain compositions for this use have been found to be azeotropic or near-azeotropic. The usefulness of heptafluoropropane in these regards has been disclosed in U.S. Pat. No. 5,124,053, issued to Iikubo on Jun. 30, 1992.

A study on the effectiveness of heptafluoropropane as an inerting compound has been reported in an article entitled Inerting of Propane-Air Mixtures with 1,1,1,2,3,3,3-Heptafluoropropane ($C_3F_7H$)—Nitrogen Blends, Zalosh et al., Chem. Phys. Processes Combust. 475–8 (1993). The study related to the use of heptafluoropropane in conjunctiong nitrogen gas to render propane-air mixtures inert.

Heptafluoropropane is also known to be useful as a propellant in certain applications. For example, Canada Patent No. 2,086,492 describes the use of heptafluoropropane as a propellant with medical aerosol formulations. The heptafluoropropane is described as a suitable replacement for the environmentally unacceptable chlorofluorocarbon propellants. Further the heptafluoropropane is indicated to be useful at lower vapor pressures, to have better pressure-seal properties, elastomer compatibility and solvent power, and to provide higher formulation stability while being non-flammable. Propellant compositions including heptafluoropropane are also disclosed in Japan Patent No. 4,332,786 for use with skin drugs, antiperspirants, deodorants, etc.; European Patent 562032 for use with inhalation devices dispensing steroid or bronchodilator compositions; and PCT Application No. WO 9322415 A1 for use with cleaning compositions for electrical devices, mirrors, plastics, etc.

A non-flammable sterilant mixture containing ethylene oxide and heptafluoropropane is described in U.S. Pat. No. 5,314,682. The mixture is indicated to be non-flammable in all concentrations of air, and may further comprise nitrogen, carbon dioxide, argon or $CHF_3$ as a propellant. The composition is disclosed to be useful for sterilizing medical equipment and rubber and plastic goods, and as fumigants for furs, bedding and paper goods.

In U.S. Pat. No. 4,971,716 there is described the use of a composition of heptafluoropropane and ethylene oxide in sterilizing applications. The composition is noted as being chemically stable, minimally segregating, compatible with objects to be sterilized, improved as to suppression of flammability, and sufficient in terms of vapor pressure.

SUMMARY OF THE INVENTION

Briefly describing one aspect of the present invention, there is provided a method for storing atmosphere sensitive products which comprises surrounding the product with an amount of heptafluoropropane effective to reduce degradation of the product due to contact with oxygen and other deleterious gases in the air. In a particular method the product is provided in a container and the amount of heptafluoropropane used is sufficient to provide a protective blanket of heptafluoropropane above the product. In a related method, the container is closed and the heptafluoropropane constitutes at least about 5%, preferably at least about 20%, and as much as 100% v/v of the headspace in the container over the product.

Another aspect of the present invention comprises a method for containing atmosphere sensitive products, including foods, pharmaceuticals, chemicals and equipment, which comprises storing the product in a container with an amount of heptafluoropropane sufficient to reduce the risk of fire or explosion. For certain products, the heptafluoropropane serves both this purpose and that of protecting the product from degradation.

DESCRIPTION OF THE PREFERRED EMBODIMENT

For the purposes of promoting an understanding of the principles of the invention, reference will now be made to the following embodiments and specific language will be used to describe the same. It will nevertheless be understood that no limitation of the scope of the invention is thereby intended, such alterations and further modifications in the invention, and such further applications of the principles of the invention being contemplated as would normally occur to one skilled in the art to which the invention relates.

It has been determined that heptafluoropropane is useful in a variety of applications to protect/preserve food products, chemicals, etc. In addition, the presence of the heptafluoropropane provides an additional advantage of reducing or eliminating the risk of fire or explosion. The heptafluoropropane is provided in the headspace for the food or chemical product. That is, the heptafluoropropane is placed into the container, package, storage facility or the like and remains in the atmosphere above and surrounding the product to be protected. The heptafluoropropane is useful in connection with any product which is "atmosphere sensitive", which for purposes herein refers to the fact that the product will be contaminated, degraded, sensitized, spoiled, or physically or chemically altered as a result of exposure to oxygen or another component of a surrounding atmosphere. The heptafluoropropane works to replace or sufficiently modify the surrounding atmosphere to reduce or eliminate the deleterious effect which would otherwise occur due to exposure to the atmosphere.

The present invention utilizes heptafluoropropane in any of its isomeric forms. Heptafluoropropane is itself available commercially, and also may be conveniently produced via such routes as the reaction of commercially available hexafluoropropene with anhydrous HF as described in U.K. Patent 902,590. This compound has an ODP (oxygen deletion potential) of zero and therefore has no effect on stratospheric ozone.

The key to long term storage for many foods, pharmaceuticals, chemicals and equipment is the avoidance or reduction of oxygen contamination or degradation. It has been determined that heptafluoropropane is useful as a non-flammable adjunct in a variety of these situations. In particular, the heptafluoropropane is used to provide a desirable non-flammable and/or non-oxygen containing atmosphere.

Many products, particularly food, pharmaceutical and chemical products, are required to be packaged for protection against oxygen contamination and degradation. In addition, the products are frequently required to remain packaged for relatively long periods of time. It has been found that providing heptafluoropropane in the surrounding atmosphere for the contained products minimizes the potential for damage to the product and the surroundings. Also, storage of raw materials prior to processing benefits from the presence of heptafluoropropane by reducing contamination, minimizing reaction with oxygen, and reducing the likelihood of losses due to fire and explosion.

In some situations, the period of storage may be unusually long. By way of example, many products are specifically packaged or stored for long periods of time. Military packaging of supplies, including for example mechanical equipment and apparatuses and explosives, as well as foods, pharmaceuticals and other chemicals, is frequently directed to long term storage of many years. Packaging and storing these items in the presence of heptafluoropropane would protect the supplies from deterioration and would provide fire extinguishing or suppression protection. National disaster supplies in long term storage would similarly benefit from the presence of heptafluoropropane.

It is well known that food and related products must be properly packaged and stored to avoid degradation due to exposure to oxygen. In addition, in some situations the presence of oxygen can present severe fire and explosion threat. It has been found that heptafluoropropane is a safe and effective compound when used in conjunction with the storage and packaging of food and food products to minimize these problems. It is also noteworthy that heptafluoropropane has advantages over certain other inert storage gases, for example nitrogen, in that heptafluoropropane has a relatively high vapor density. As a result, the heptafluoropropane will tend to remain in a container even after the container is opened or develops a leak at the top. This is in contrast to nitrogen, which has essentially the same vapor density as air and may be easily lost from a container which has been opened or has developed a leak.

In use with food and food products, the heptafluoropropane is placed in the surrounding atmosphere. Any manner effective to retain the heptafluoropropane in the proximity of the products is suitable. For example, in common situations the food items will be stored in cans, bottles or similar storage containers. The heptafluoropropane is simply added to the container to displace the air which would otherwise be present, and the container is then sealed. The amount of heptafluoropropane will vary with the application. In general, a sufficient amount of heptafluoropropane is added to at least provide a layer of the heptafluoropropane around and over the product. It will usually be convenient and preferable to simply fill essentially all of the container with heptafluoropropane. However, it may also be suitable to include only a portion of heptafluoropropane in the atmosphere surrounding the food product. In one aspect, the amount used is sufficient to provide a flame-suppressed atmosphere over the product, thereby minimizing the risk of fire or explosion, particularly in those situations where this would otherwise be a significant risk. Depending on the circumstances, at least about 5% v/v (volume of heptafluoropropane per volume of atmosphere), and more preferably at least about 20% of the atmosphere surrounding the food product is heptafluoropropane. Further desirable effects are achieved when using at least about 50% heptafluoropropane.

Related to the foregoing is the use of heptafluoropropane in connection with the storage of bulk food products, particularly grains, flours, etc. Examples of storage situations in which heptafluoropropane may be used would include grain silos and large storage containers, particularly closed receptacles, for storage of flour and the like. The heptafluoropropane is introduced into the storage facility for these products and maintained at the desired level. Introduction of the heptafluoropropane may occur as a one time addition, or may be periodic or continuous, depending on the circumstances. The method used is selected to maintain the desired amount of heptafluoropropane in the storage facility.

As indicated previously, the amount of heptafluoropropane provided is dependent on the nature of the product and the effect desired. In one aspect, a sufficient amount of heptafluoropropane is maintained in the atmosphere surrounding the bulk product to reduce fire and explosion hazards. In this regard, the heptafluoropropane is preferably maintained at a level of at least about 5% v/v, and more preferably at least about 20% v/v. In another aspect, the heptafluoropropane is utilized to reduce contact of the bulk food product with oxygen or other deleterious gases. According to one approach, an amount of heptafluoropropane is used which is sufficient to provide heptafluoropropane surrounding and overlying the bulk product. Another approach is to maintain an effective amount by volume percent to reduce degradation by oxygen, etc., which amount is preferably at least about 5% v/v, and more preferably at least about 20% v/v. Of course, even higher percentages of heptafluoropropane, for example at least about 50% v/v, will have the same or greater utility depending on the circumstances. Where practicable, such as in essentially closed storage facilities, and particularly where risk of degradation and/or fire/explosion is especially high, the heptafluoropropane is maintained as essentially 100% of the surrounding atmosphere within storage facility. Of course, the amount of heptafluoropropane used will be limited in those situations where the atmosphere must be breathable, in which case the amount of heptafluoropropane in the air is preferably less than about 9% v/v, and more preferably about 5%. This volume composition complies with the EPA Snap Rule, Federal Register Mar. 18, 1994, part II, volume 59, no. 53, page 13159, which defines a cardiotoxic No Observable Adverse Effect Level (NOEL) of greater than 9% v/v. Compositions may be used up to 99% v/v if exposure times are less than thirty seconds.

It has further been found that heptafluoropropane is useful in conjunction with the storage of chemicals, including pharmaceuticals, to protect against adverse effects due to the presence of oxygen or other gases in the air. Again, the heptafluoropropane is used to surround the chemicals to prevent degradation upon contact with gases, and/or to reduce fire and explosion potential. The use of heptafluoropropane is particularly well suited to chemicals stored in closed containers, especially where the storage will be maintained for extended periods of time.

The heptafluoropropane is used with chemicals to protect against degradation by in effect insulating the chemicals from the air. The heptafluoropropane is provided in an amount sufficient to surround the chemicals, i.e., by at least covering the chemicals and providing a protective layer over them. Therefore, the amount of heptafluoropropane used is that amount which will provide a covering layer over the chemicals. It will usually be preferred to fill the containers for such chemicals with essentially 100% heptafluoropropane. However, lesser amounts of heptafluoropropane may be used ranging preferably from at least about 5% v/v, and more preferably from at least about 20% v/v. Concentrations of at least about 50% will provide the same or additional advantages, particularly for products having greater potential for fire or explosion.

Because of the higher vapor density of heptafluoropropane, the use of heptafluoropropane has an advantage over other inert gases such as nitrogen. The vapor headspace above an oxygen-sensitive compound, for example requires only partial displacement of the surrounding air with heptafluoropropane to ensure complete protection from reaction with atmospheric oxygen. This is due to the heavier-than-air density of heptafluoropropane, which provides a gaseous "floating lid" which negates the need to completely displace all of the headspace air as required with nitrogen gas storage. In addition, the heavy density of heptafluoropropane will diminish or eliminate any diffusion of heptafluoropropane into the air headspace above a compound under storage, which again contributes to a very effective blanketing effect of heptafluoropropane.

It will be noted that the heptafluoropropane is useful in connection with chemicals which are dispensed from the bottom of a container. As a liquid chemical is dispensed from its container, air will enter in the headspace over the liquid. However, the heptafluoropropane will move down with the lowering liquid level, maintaining the protective blanket over the chemical and continuing to protect it from the air.

Protection from fire and/or explosion is also achieved by the use of heptafluoropropane with stored chemicals. Of course, many chemicals may present a hazard when contained in exposure to oxygen in the air. The presence of heptafluoropropane within the container is useful to provide a barrier between the chemical and the air to reduce this risk. Therefore, an amount of heptafluoropropane within the container is provided to at least provide a blanket of heptafluoropropane over the chemical. In a particular aspect, the heptafluoropropane is present in an amount of at least about 5% v/v of the air, and more preferably at least about 20% v/v. Depending on the nature of the contained chemical, the preferred amount of heptafluoropropane may be higher or lower, and for example may preferably be at least about 50% v/v.

In addition, the presence of heptafluoropropane may reduce the potential for fire and/or explosion upon opening or leakage of the chemical from a storage container. As the chemical is released from the container, the associated release of heptafluoropropane will suppress the possibility of a fire or explosion in the immediate vicinity until the chemical is more dispersed.

Heptafluoropropane could be added, for example, to the headspace to provide protection against oxygen degradation, fire and potential explosions originating in the headspace of large fuel storage tanks and vessels. This would apply, for example, to the U.S. Strategic Petroleum Reserve system (600 million barrels in 1995), as well as world-wide storage facilities. This would also apply to any fuel or gasoline storage vessels at refineries, distribution terminals, and industrial plants. In the case of local and small scale storage tanks such as those present in gasoline refueling stations, heptafluoropropane could be added to the headspace of underground storage tanks to provide fire and explosion protection as described. In the case where fuel has already ignited and is burning on the surface of a storage tank or vessel, heptafluoropropane could be introduced at a subsurface level in such quantity as to have it migrate to the surface of the flammable liquid and thereby break the interface and contact of oxygen with the flammable liquid and subsequently extinguish the flame.

The present invention also contemplates the use of blends of heptafluoropropane with other gases where applicable. In those instances in which the heptafluoropropane is used to reduce fire or explosion hazard, it is suitable to blend the heptafluoropropane with other inert gases or with fire extinguishants compatible with the application. For situations in which the heptafluoropropane is used to reduce degradation due to atmospheric oxygen or other gases, then it is contemplated that the heptafluoropropane may be blended with other inert gases. For example, if oxygen degradation is the concern, then it may be suitable to blend the heptafluoropropane with nitrogen for the purpose of reducing cost or for other indicated reasons. In such instances, it may be desirable to maintain the heptafluoropropane at a level which provides other advantageous effects, such as the reduction of fire or explosion potentials where existent.

EXAMPLE 1

Heptafluoropropane is injected into the headspace of a food product container. The food product is one which readily identified as atmosphere sensitive, for example dairy products, breads and most all other canned or otherwise packaged foods. Providing about 5% heptafluoropropane in the atmosphere surrounding the contained food product reduces the degradation of the food product. Similar testing with 20%, 50% and 100% heptafluoropropane also reduces degradation of the food product, generally with correspondingly increasing effect.

EXAMPLE 2

Pharmaceutical products which are atmosphere sensitive, including various tablet and capsule preparations and parenterals are protected by being surrounded with an atmosphere containing at least a portion of heptafluoropropane. The addition of levels of heptafluoropropane at 5%, 20%, 50% and 100% v/v in the headspace over the contained pharmaceuticals reduces the deleterious effects of oxygen and other components of normal atmosphere, thereby increasing the integrity of the product and extending its shelf life.

EXAMPLE 3

Similar tests for various atmosphere sensitive chemicals yield similar results. Heptafluoropropane is injected into the headspace of the chemical container to provide a protective gaseous floating lid. The presence of heptafluoropropane at the indicated levels of 5%, 20%, 50% and 100% provides generally increasing efficacy in protecting the chemicals from degradation.

EXAMPLE 4

The use of heptafluoropropane for the cited purposes is also demonstrated for bulk stored products, including foods, pharmaceuticals and other chemicals, including fuels and commercial explosives and explosive materials and pyrophoric materials, and packaging of said materials. Results similar to those cited in Examples 1–3 are achieved. In particular, protection from the atmosphere is obtained while the use of levels 5% and 9% heptafluoropropane provide atmospheres which are breathable.

EXAMPLE 5

The use of heptafluoropropane for the cited purposes is also demonstrated for bulk stored products, including mechanical equipment and apparatuses, electrical and electronic equipment, and military packaging of said equipment. Results similar to those cited in Examples 1–4 are achieved. In particular, protection from the atmosphere is obtained while the use of levels 5% and 9% heptafluoropropane provide atmospheres which are breathable.

While the invention has been illustrated and described in detail in the foregoing description, the same is to be considered as illustrative and not restrictive in character, it being understood that only the preferred embodiments have been shown and described and that all changes and modifications that come within the spirit of the invention are desired to be protected.

What is claimed is:

1. A method for storing atmosphere sensitive food grains which comprises surrounding said food grains with an atmosphere containing at least about 5% v/v up to 100% v/v heptafluoropropane.

2. The method of claim 1 in which the atmosphere contains at least about 20% v/v heptafluoropropane.

3. The method of claim 2 in which the atmosphere contains at least about 50% v/v heptafluoropropane.

4. The method of claim 3 in which the atmosphere contains about 100% v/v heptafluoropropane.

5. The method of claim 1 which includes storing the food grains in a closed container having a headspace over the food grains, and which includes providing an atmosphere in the headspace over the food grains containing at least about 5% v/v up to 100% v/v heptafluoropropane.

6. The method of claim 5 in which the atmosphere contains at least about 20% v/v heptafluoropropane.

7. The method of claim 5 in which the atmosphere contains at least about 50% v/v heptafluoropropane.

8. The method of claim 5 in which the atmosphere contains about 100% v/v heptafluoropropane.

9. The method of claim 1 in which said surrounding comprises forming a blanket of heptafluoropropane on top of said product.

10. The method of claim 1 in which the food grain is flour.

* * * * *